United States Patent [19]

Claypool

[11] Patent Number: 4,929,828
[45] Date of Patent: May 29, 1990

[54] INSPECTING GLASS CONTAINERS FOR LINE-OVER FINISH DEFECTS WITH BIFURCATED FIBER OPTIC BUNDLE

[75] Inventor: Mark P. Claypool, Horseheads, N.Y.

[73] Assignee: Emhart Industries, Inc., Hartford, Conn.

[21] Appl. No.: 161,623

[22] Filed: Feb. 29, 1988

[51] Int. Cl.⁵ .............................. G01N 9/04; B07C 5/00
[52] U.S. Cl. ............................. 280/223 B; 250/227.29; 209/524
[58] Field of Search .......................... 250/223 B, 227; 356/240; 209/526, 524; 350/96.25, 96.26, 96.27

[56] References Cited

U.S. PATENT DOCUMENTS

| | | | |
|---|---|---|---|
| 3,098,564 | 7/1963 | Fouse et al. | 209/526 |
| 3,176,842 | 4/1965 | Fry | 209/526 |
| 3,349,906 | 10/1967 | Calhoun et al. | 250/223 B |
| 3,639,067 | 2/1972 | Stephens | 356/240 |
| 3,739,184 | 6/1973 | Katsumata et al. | 356/240 |
| 3,851,975 | 12/1974 | Serret | 250/223 B |
| 3,880,750 | 4/1975 | Butler et al. | 209/111.7 |
| 4,027,982 | 6/1977 | Ohishi | 250/561 |
| 4,488,648 | 12/1984 | Claypool | 209/526 |
| 4,498,003 | 2/1985 | Cibis | 250/223 B |
| 4,672,200 | 6/1987 | Claypool et al. | 250/227 |

FOREIGN PATENT DOCUMENTS 477428  6/1975  Australia .......................... 250/223 B

*Primary Examiner*—David C. Nelms
*Assistant Examiner*—Michael Messinger
*Attorney, Agent, or Firm*—Spencer T. Smith

[57] ABSTRACT

Apparatus for detecting line-over defects at the finish of a glassware container. A bifurcated fiber optic bundle includes sender and receiver fiber branches; one of the branches terminates at a modulated visible red high intensity LED light source, the other at a photosensor. The non-bifurcated, probe end of the fiber optic cable terminates in a rectangular pattern of sending and receiving fibers in a random mix. The probe end of the fiber optic bundle is positioned directly over the container finish and pointed straight down. An intervening lens assembly produces a focused 1:1 image of the rectangular pattern at the bottle finish with the long axis of the rectangle oriented radially across the finish. An electronic assembly modulates the LED, demodulates the photodetector output, and detects sharp reductions in the intensity of light reflected back to the receiver fibers, indicative of line-over defects.

19 Claims, 4 Drawing Sheets

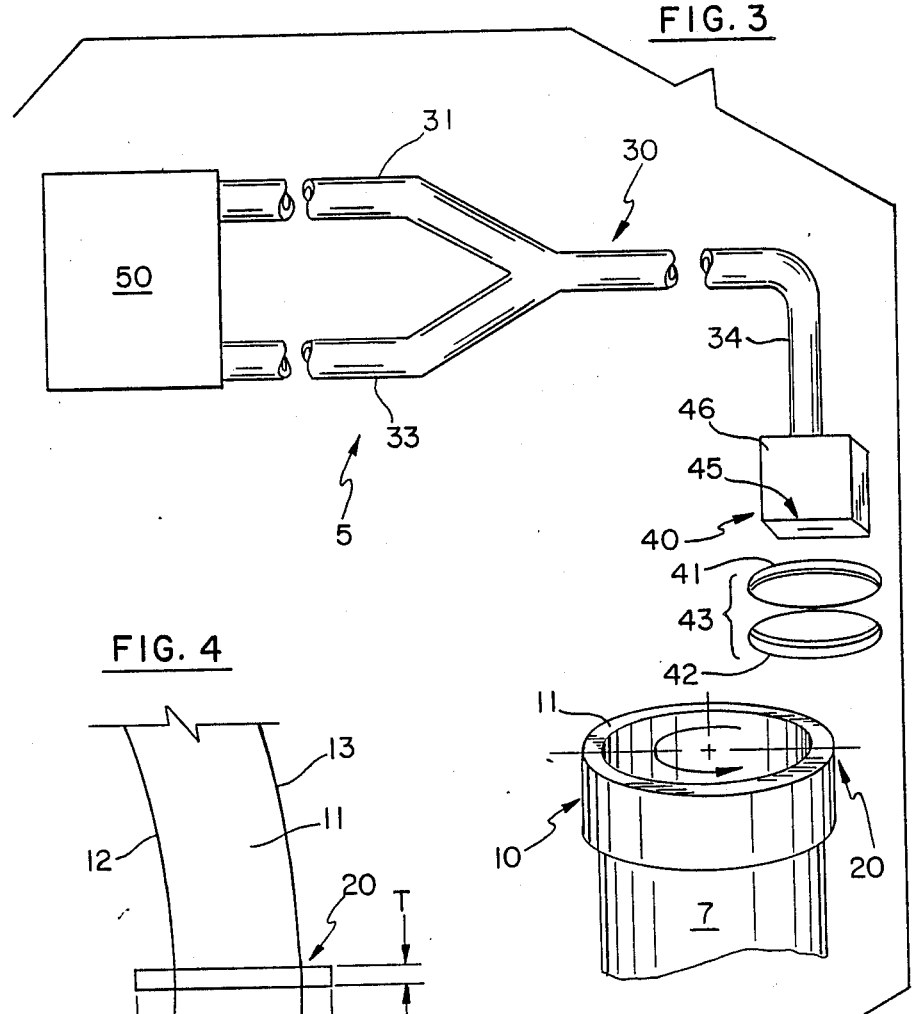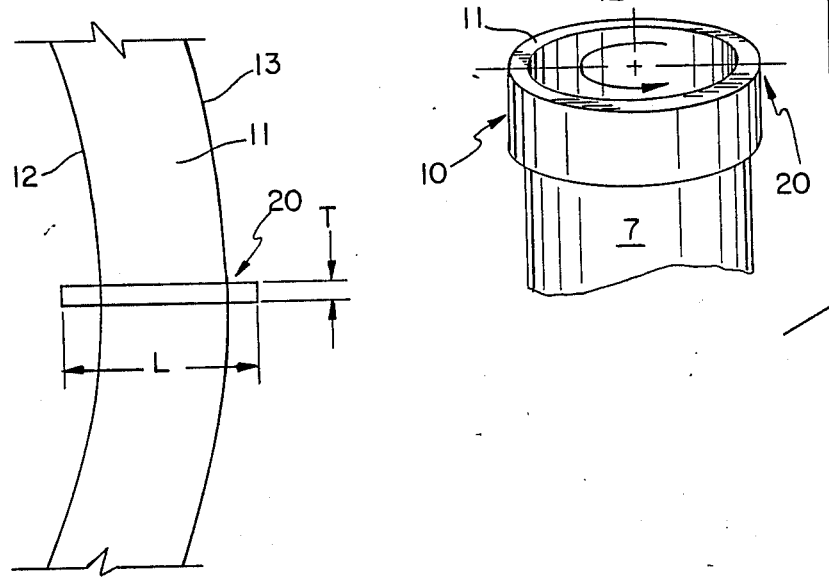

INSPECTING GLASS CONTAINERS FOR LINE-OVER FINISH DEFECTS WITH BIFURCATED FIBER OPTIC BUNDLE

BACKGROUND OF THE INVENTION

The present invention relates to the detection of line-over defects at the finish of glassware containers, and more particularly to the use of optical apparatus for this purpose.

The so-called "line-over" defect is a common problem in the manufacture of glass containers; other common names for line-overs are "shear marks" and "nit marks". This defect is a very small groove which extends radially across the sealing surface of the finish of the glass container; see FIG. 1. It has been considered one of the worst and hardest to detect defects throughout the industry. In carbonated beverages, for example, the cap seal is not capable of sealing these fine grooves, and over a period of time, the carbonation gases seep out and the beverage goes flat. Food jars are another critical area. If the seal is bad due to this defect, the food can become contaminated. The baby food industry is particularly concerned with line-overs.

It is believed that this groove is caused by a line of cold glass left on the molten gob of glass where the previous gob was sheared as the glass streams from the feeder through the shears. See, for example, U.S. Pat. No. 4,515,002.

In recent years, many attempts have been made to develop equipment to sense line-over defects in glass containers in order to reject bad bottles from the production line with a high degree of accuracy. Most such devices cause an undesirably large number of good ware to be rejected while still missing a considerable percentage of defective containers. Prior art approaches have included mechanical sensing arrangements such as those disclosed in U.S. Pat. Nos. 3,879,993 and 3,395,573. A wide variety of optical approaches have also been taken. One approach uses specular, focused light directed at the finish of the container from within, wherein the presence of line-over defects will cause the focused light to be refracted in a direction different from that in the absence of a defect, this deflection being detected by strategically placed photosensors. See, for example, U.S. Pat. Nos. 3,302,787 and 3,107,011. Another approach, disclosed in U.S. Pat. No. 4,606,634, uses a planar source of diffuse light, a video camera being used to produce an image of any line-over defects.

A third approach, generally of the type adopted in the present invention, uses light downwardly directed at the sealing surface, and detects reflected light in order to sense whether or not a line-over defect is present. The system of U.S. Pat. No. 3,880,750 focuses an intense spot of incandescent light across the container rim, and uses an optical sensor assembly to receive reflected light, together with processing electronics to detect departures from a normal light signal. Frequency filtering of the photodetector signal removes the normal light signal and provides individual signals for different defect types. The light source and photodetector assemblies are located at complementary acute angles relative to the plane of the sealing surface.

Another patent which discloses a system utilizing the reflected-light approach, commonly assigned with the present application, is U.S. Pat. No. 4,488,648. This patent preferably utilizes a DC light source at an acute angle relative to the sealing surface, the photodetector assembly also being located at an acute angle. (See FIG. 8.) A line-over defect produces a reduction in light - a "dark spot". Both this system and the '750 discussed above did not successfully solve certain problems posed by the use of reflected light for line-over defect detection. The sidewall angle of line-over grooves is completely unpredictable. One wall's angle may be steep while the opposing wall is shallow. It is difficult to reliably reflect light back onto a sensor from these defects as they vary from one container to the next and are very unpredictable. FIGS. 2A, 2B, and 2C illustrate three typical line-over groove orientations, as seen from the bottle interior. Further problems with this reflected light approach include dirt, dust, and rough finish surfaces that can cause light to be reflected back to the sensor as well.

Accordingly, it is a principal object of the invention to provide a more accurate line-over detection system of the optical type. A related object is to improve the percentage of line-over defects which are detected. Another related object is to reduce the percentage of "false positives", for example, due to dust, dirt, and rough finish surfaces.

SUMMARY OF THE INVENTION

In furthering the above and additional objects, the invention utilizes a fiber optic scanning head downwardly directed at the finish of a glass container, such scanning head comprising a bifurcated fiber optic bundle together with cooperating optical and electronic components. The bifurcated fiber optic bundle has sender and receiver portions respectively containing sender and receiver optical fibers, and a joined portion containing both sets of fibers terminating at a probe end. Such fiber optic bundle has a light source for illuminating the sender fibers at one of the bifurcations, and a photodetector device at the other bifurcation for producing an output signal representative of the intensity of light transmitted by the receiver fibers. The scanning head further includes a lens system which transmits light emitted from the sender fibers at the probe end straight down toward the container finish, and which receives reflections from the finish some of which are captured by the receiver fibers at the probe end. The probe end is configured in an elongated pattern, which pattern is imaged by the lens system onto the sealing surface in a pattern extending radially across the finish.

In accordance with a preferred embodiment of the invention, the probe end is configured in an elongated rectangle, which pattern is imaged onto the container finish with the long axis extending radially across the sealing surface. Preferably, the lens system images this pattern slightly out of focus onto the sealing surface. The fiber optic fibers at the probe end advantageously are intermingled in a random bundle (random fiber pattern of sender and receiver fibers).

Another aspect of the invention relates to the light source and photodetector optics and electronics. The light source preferably comprises a high intensity visible LED, most preferably in the red part of the spectrum. To avoid interference with ambient light this LED can be modulated, and the photodetector output demodulated to produce an analog signal representative of the intensity of detected light. By scanning the container finish while rotating either the container or scanning head, the system can thus provide a wave form representative of the variations of intensity of detected light over a scanning period which may encompass the entire sealing surface. This inspection technique has been observed to effectively discriminate between line-over fractures, which produce relatively pronounced peaks, and dust, dirt, or rough spot features, as well as background noise. This signal may be further processed and used to selectively reject containers.

BRIEF DESCRIPTION OF THE DRAWINGS

The above and additional aspects of the invention are illustrated in the detailed description of the preferred embodiment which follows, taken in conjunction with the drawings in which:

FIG. 2A shows a groove with a steep right wall, shallow left wall;

FIG. 2B shows a groove with a symmetrical profile;

FIG. 2C shows a groove with a shallow right wall, steep left wall;

FIG. 3 is a somewhat schematic view of an overall inspection system in accordance with a preferred embodiment of the invention, scanning a bottle finish in counterclockwise rotation;

FIG. 4 is a partial plan view of a container sealing surface seen from above, showing the rectangular light image of the inspection system of FIG. 3;

FIG. 6A shows a typical signal-to-noise wave form;

FIG. 6B shows an expanded view of scan including a line-over defect signal; and

FIG. 6C shows a wave form featuring both a line-over signal and dust signals.

DETAILED DESCRIPTION OF THE PREFERRED EMBODIMENT

Figure 1:
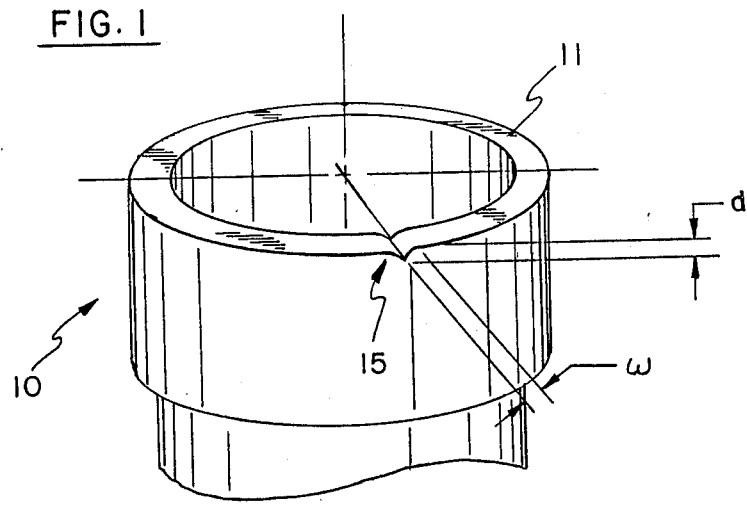
FIG. 1 is a perspective view of a glass bottle finish, with a line-over groove.
Figures 2A, 2B, 2C:
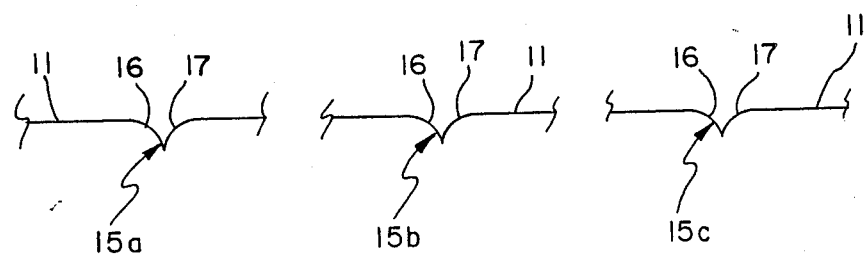
FIGS. 2A, 2B, and 2C are partial elevation views of a glass container finish, viewed from the interior, with three different line-over groove orientations.

FIG. 3 illustrates the construction of an inspection device 5 in accordance with the preferred embodiment of the invention. Inspection assembly 5 includes a fiber optic probe 30 trained on the finish 10 of a glass container 7. In the illustrated embodiment, container 7 is caused to rotate relative to probe 30 so that probe 30 performs a complete circumferential scan of the sealing surface 11. Fiber optic probe 30 includes, bifurcations 31, 33 and a joined portion 34. Bifurcation 31 includes sender fibers; bifurcation 33 carries receiver fibers; and joined portion 34 has the sender and receiver fibers intermingled terminating at a probe end 40 at which the fibers are thoroughly intermixed in a random distribution. The probe end 40 is carried in a probe mount 46 and terminates at an elongated rectangular slit 45. Probe mount 46 is set up to align and orient the fiber optic bundle end 45 over the sealing surface 11 to form an elongate image 20 directly below. 1:1 lens assembly 43, comprising lenses 41 and 42, advantageously creates a slightly out-of-focus image 20 of the probe end 45 across sealing surface 11. It is desirable to provide a slightly out of focus image so that the reflections from the sealing surface return to both the sender and receiver fibers at probe end 40, rather than just to the sender fibers.

Now having reference to the partial plan view of the sealing surface 11 shown in FIG. 4, the probe end image 20 comprises an elongate rectangle having a length L and width T. The dimension L is somewhat greater than the thickness between the inner wall 12 and outer wall 13 of container finish 10. In an operative embodiment of the invention, L equalled 0.154 inches and T equalled 0.012 inches. This value of L was chosen to accommodate most common thicknesses of glass bottle finishes, and of T to yield a good signal-to-noise ratio. Rectangular image 20 is oriented with its long axis along a radius of the sealing surface 11.

Figure 5:
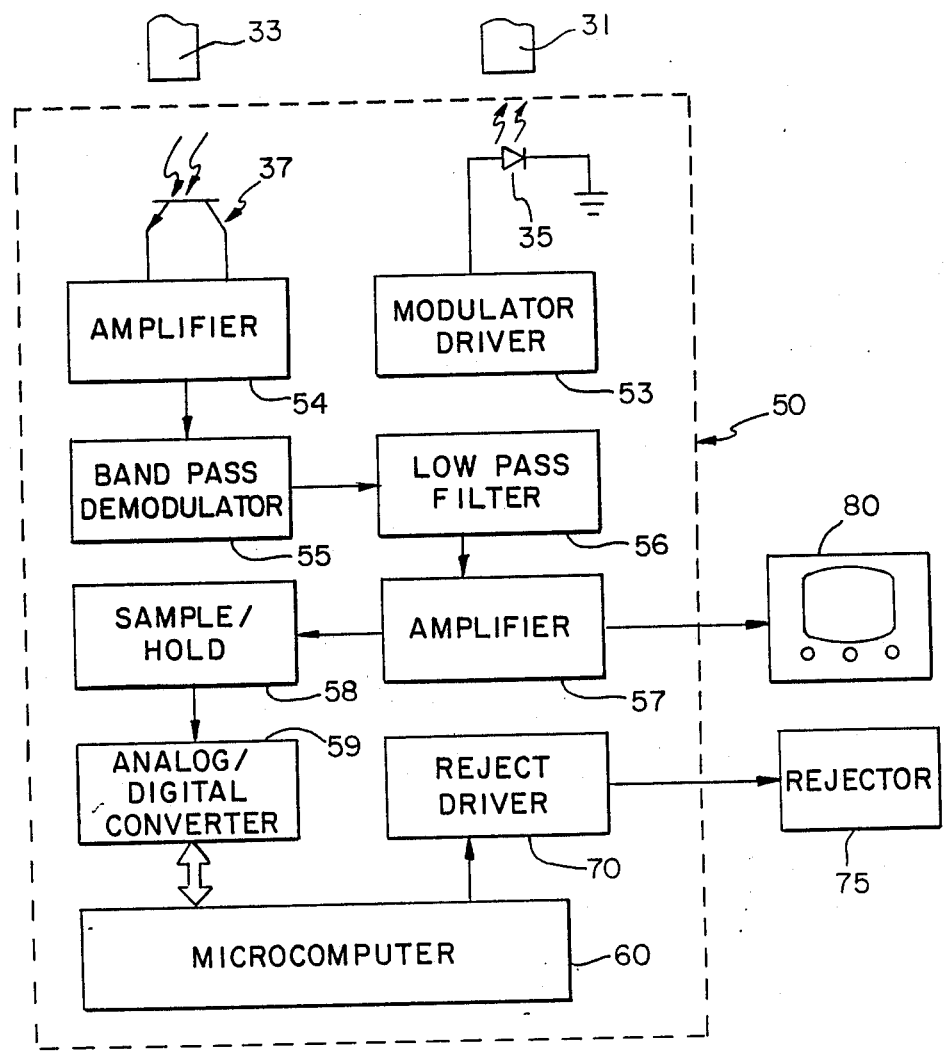
FIG. 5 is a schematic diagram of the light source, photodetector, and associated electronics, from the system of FIG. 3.

FIG. 5 schematically illustrates a set of components for the signal processing electronics 50 of FIG. 3. The light source for transmitting fiber 31 is a high intensity visible LED 35, in the red part of the visible spectrum. LED light source devices may be modulated at different frequencies, and provide a continuous, high-intensity output with minimum drift, over a prolonged service life. It should be understood that other light sources may be employed, taking into account the optical characteristics of the container finish 10. The photo receiver 37 is a phototransistor device which was matched in spectral response to LED 35. The phototransistor output, amplified at 54, is demodulated by band pass filter 55 calibrated to pass the modulation frequency of the red visible light LED 35. Low pass filter 56 extracts the slope signal from the modulated carrier signal, which slope signal is amplified at 57. The amplified slope signal is fed to sample/hold circuit 58 and thence to analog-to-digital converter 59 which integrates and digitalizes this signal for each sample point. A microcomputer 60 analyzes the integrated slope signal from circuit 50 as such signal is compiled for rotating container 7. Microcomputer 60 may in appropriate cases actuate reject device 75 via reject driver 70 to reject the container 7 when the processed information for that container indicates the presence of an unacceptable line-over defect.

The inspection system 5 works as follows. Modulated LED light travels down the sending fibers and is imaged slightly out-of-focus by lens assembly 43 onto the sealing surface 11 of finish 10. This light is reflected back up through the lens assembly 43 onto the sending and receiving random fiber pattern 45. The receiving fibers carry the light back to photosensor 37, where as described above the photosensor signal is demodulated to create an analog signal based upon the amount of light reflected back from the finish. As container 7 rotates axially below probe 30, the entire sealing surface 11 is scanned by this device. The result is a signal representative of the reflection pattern of the entire sealing surface 11. As a line-over passes through the image 20, light is reflected in many different directions and very little will return through the lensing system 43. This will cause a significant drop in signal level. Dust, dirt, and rough finish areas can also reduce the light reflected back, but as illustrated below with reference to FIGS. 6A–6C, the use of a radially oriented long, narrow light pattern 20 markedly improves the response of the inspection system 5 to line-over defects while discriminating such defects from other causes of signal reduction.

Figure 6A:
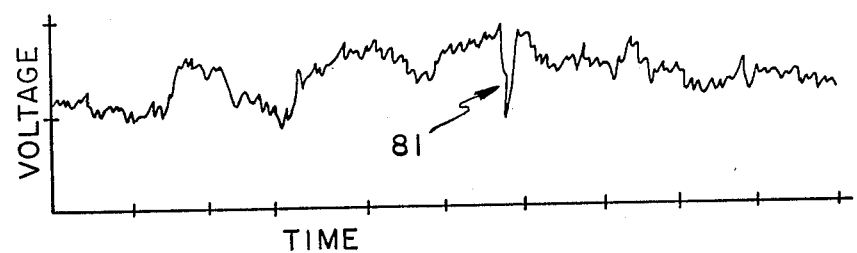
FIG. 6A, 6B, and 6C are plots of a processed photodetector output signal representing the intensity of detected light, over a scan of the entire container finish.
Figure 6B:
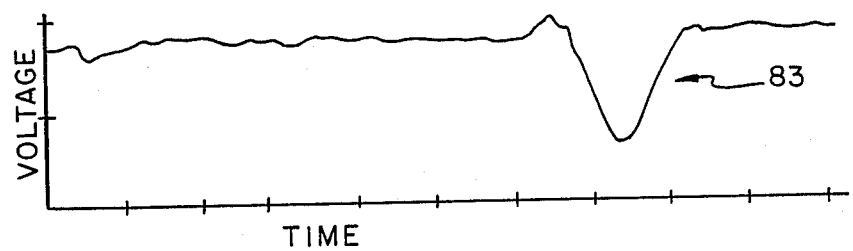
Figure 6C:
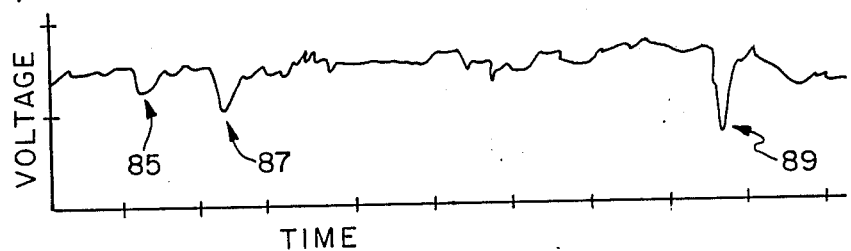

FIGS. 6A–6C are various plots or displays of an analog signal produced by the processing electronics 50 representing the amount of LED light reflected back through the fiber optic bundle 30 over various points of a scanning interval. The waveforms of FIGS. 6A–6C were displayed at an oscilloscope 80 which received the output of amplifier 57 from the circuit 50 of FIG. 5. The plot of FIG. 6A illustrates a typical signal-to-noise waveform including a dip at 81 caused by the passage of a line-over defect under the fiber optic probe 30. The plot of FIG. 6B shows a signal reduction 83 created by a line-over defect after expanding the scale of the plot to 500 microseconds per division as compared with 10 milliseconds per division for the plot of FIG. 6A. FIG. 6C shows a plot taken at 2.5 milliseconds per division in which dips 85 and 87 were caused by dust particles, while signal drop 89 was caused by a line-over defect. It will be seen that the line-over defect caused a much sharper drop in signal level. The plot of FIGS. 6A–6B illustrate the capability of line-over inspection system 5 to selectively and repeatedly detect true line-over defects while minimizing good ware lost due to other finish marks that are not considered problems.

While reference has been made above to a specific embodiment, it will be apparent to those skilled in the art that various modifications and alterations may be made thereto without departing from the spirit of the present invention. Therefore, it is intended that the scope of this invention be ascertained by reference to the following claims.

I claim:

1. Apparatus for optically inspecting the sealing surface of glass containers, comprising:
   a scanning head, comprising a bifurcated fiber optic bundle including sender and receiver bifurcations respectively containing sender and receiver optical fibers, and a joined portion containing said sender and receiver fibers, said joined portion terminating at a probe end;
   a light source for illuminating the sender fibers;
   a lens system for imaging the light emitted from the probe end onto said sealing surface, and for transmitting light reflected by said sealing surface toward said probe end; and
   processing means for producing output signals essentially representative of the intensity of light transmitted by the receiver fibers;
   said sealing surface substantially defining a plane, and the probe end located substantially along a perpendicular to the sealing surface plane at the location where said light from the probe end is imaged on said surface.

2. Apparatus as defined in claim 1, further comprising processing means for registering when the output signals fall below a preselected threshold value.

3. Apparatus as defined in claim 1, wherein the probe end is configured in an elongate pattern, and the lens system images the elongate pattern onto the sealing surface with a long axis of the pattern oriented radially at the sealing surface.

4. Apparatus as defined in claim 3 wherein the elongate pattern comprises a rectangle.

5. Apparatus as defined in claim 3 wherein the sealing surface is annular with inner and outer edges and the image of the elongate pattern extends beyond the inner and outer edges of the sealing surface.

6. Apparatus as defined in claim 1 wherein the probe end pattern is imaged onto the sealing surface slightly out of focus.

7. Apparatus as defined in claim 1 wherein the light source comprises a high-intensity visible light LED.

8. Apparatus as defined in claim 7 wherein the LED visible light wave lengths are concentrated in the red part of the visible spectrum.

9. Apparatus as defined in claim 1, for providing a circumferential inspection of a container sealing surface, further comprising means for causing the rotation of one of said container and said scanning head relative to the other whereby said scanning head circumferentially scans said sealing surface.

10. Apparatus as defined in claim 1, wherein the fiber optic bundles each include approximately equal numbers of sender and receiver fibers, which are randomly intermingled at the probe end of said bundle.

11. Apparatus as defined in claim 1, wherein the light source provides amplitude-modulated light at a selected frequency, and the processing means includes a photodetector device for producing light intensity output signals, and means for demodulating said light intensity output signals.

12. Apparatus for optically inspecting the sealing surface of glass containers, comprising:
   a scanning head, comprising a bifurcated fiber optic bundle including sender and receiver bifurcations respectively containing sender and receiver optical fibers, and a joined portion containing said sender and receiver fibers terminating in an elongate pattern at a probe end;
   a light source for illuminating the sender fibers;
   a lens system for imaging the light emitted from the probe end onto said sealing surface essentially along a perpendicular to a plane defined by said sealing surface, and for transmitting light reflected by said sealing surface toward said probe end;
   means for producing output signals essentially representative of the intensity of light transmitted by the receiver fibers.

13. Apparatus as defined in claim 12, wherein the light source provides amplitude-modulated light at a selected frequency, and the means for producing includes a photodetector device for producing a light intensity output signal, and means for demodulating said light intensity output signal.

14. Apparatus as defined in claim 12, wherein the lens system images the elongate pattern of the probe end onto the sealing surface with a long axis of the pattern oriented radially at the sealing surface.

15. Apparatus as defined in claim 12 wherein the elongate pattern comprises a rectangle.

16. Apparatus as defined in claim 12 wherein the probe end pattern is imaged onto the sealing surface slightly out of focus.

17. Apparatus as defined in claim 12 wherein the light source comprises a high-intensity visible light LED.

18. Apparatus as defined in claim 17 wherein the LED visible light wave lengths are concentrated in the red part of the visible spectrum.

19. Apparatus as defined in claim 12, wherein said fiber optic bundles each include approximately equal numbers of sender and receiver fibers, which are randomly intermingled at the probe end of said bundle.

* * * * *